US008658188B2

(12) United States Patent
Stark et al.

(10) Patent No.: US 8,658,188 B2
(45) Date of Patent: Feb. 25, 2014

(54) RADIO-OPAQUE BIOACTIVE GLASS MATERIALS

(75) Inventors: Wendelin Jan Stark, Zurich (CH); Dirk Mohn, Ermatingen (CH); Matthias Zehnder, Zurich (CH); Thomas Imfeld, Stafa (CH)

(73) Assignees: Eth Zurich, Zurich (CH); Universitat Zurich, Zurich (CH)

( * ) Notice: Subject to any disclaimer, the term of this patent is extended or adjusted under 35 U.S.C. 154(b) by 0 days.

(21) Appl. No.: 13/390,945

(22) PCT Filed: Aug. 17, 2010

(86) PCT No.: PCT/CH2010/000200
§ 371 (c)(1),
(2), (4) Date: Feb. 28, 2012

(87) PCT Pub. No.: WO2011/020204
PCT Pub. Date: Feb. 24, 2011

(65) Prior Publication Data
US 2012/0148646 A1    Jun. 14, 2012

(30) Foreign Application Priority Data

Aug. 19, 2009  (EP) .................................. 09010656

(51) Int. Cl.
| A61K 9/14 | (2006.01) |
| A61P 31/00 | (2006.01) |
| A61P 1/02 | (2006.01) |
| A61K 6/02 | (2006.01) |
| A61K 33/08 | (2006.01) |
| B82Y 30/00 | (2011.01) |

(52) U.S. Cl.
USPC ............. 424/401; 424/400; 424/49; 424/688; 428/402; 428/403; 106/35; 977/773; 977/840; 977/919; 977/915

(58) Field of Classification Search
None
See application file for complete search history.

(56) References Cited

U.S. PATENT DOCUMENTS

| 3,911,581 A | 10/1975 | Dietz |
| 7,335,250 B2 * | 2/2008 | Burtscher et al. ............... 106/35 |
| 2003/0113686 A1 | 6/2003 | Jia et al. |
| 2006/0057213 A1 * | 3/2006 | Larhrib et al. ................ 424/489 |
| 2008/0086199 A1 * | 4/2008 | Dave et al. .................... 623/1.42 |
| 2008/0160206 A1 | 7/2008 | Burtscher et al. |
| 2009/0208428 A1 * | 8/2009 | Hill et al. ........................ 424/52 |
| 2009/0317772 A1 * | 12/2009 | Rusin et al. ................ 433/217.1 |
| 2010/0035214 A1 * | 2/2010 | Reynaud et al. .............. 433/220 |
| 2010/0226856 A1 * | 9/2010 | Vitaliano et al. ............... 424/9.1 |
| 2011/0182995 A1 | 7/2011 | Asgary |

FOREIGN PATENT DOCUMENTS

| DE | 10 2006 045 628 A1 | 4/2008 | | |
| WO | 2005/075348 | 8/2005 | | |
| WO | 2005/087660 | 9/2005 | | |
| WO | 2008/049242 | 5/2008 | | |
| WO | WO 2008/049242 | * 5/2008 | ............. | A61L 27/48 |
| WO | 2008/102214 | 8/2008 | | |
| WO | WO 2008/102214 | * 8/2008 | ............... | A61C 5/02 |

OTHER PUBLICATIONS

Mohn et al. "Radio-opaque nanosized bioactive glass for potential root canal application: evaluation of radiopacity, bioactivity and alkaline capacity", International Endodontic Journal, 43, 2010 pp. 210-217. ( Mar. 2007).*
Madler et al. "Bismuth Oxide Nanoparticles by Flame Spray Pyrolysis" J. Am. Ceram. Soc. 85[7] 1713-18 (2002).*
International Search Report for corresponding International Application No. PCT/CH2010/000200 mailed Oct. 10, 2010.
Mohn et al., "Radio-opaque nanosized bioactive glass for potential root canal application: evaluation of radiopacity, bioactivity and alkaline capacity", International Endodontic Journal, 43, 2010, pp. 210-217.
Brunner et al., "Glass and bioglass nanopowders by flame synthesis", The Royal Society of Chemistry 2006, Chem. Commun., 2006, pp. 1384-1386.
Madanat et al., "Radio-opaque bioactive glass markers for radiostereometric analysis", Acta Biomaterialia 5, 2009, pp. 3497-3505.
Waltimo et al., "Fine-tuning of Bioactive Glass for Root Canal Disinfection", Research Reports, Biomaterials & Bioengineering, J Dent Res 88(3), 2009, pp. 235-238.
Grass et al., "Flame spray synthesis under a non-oxidizing atmosphere: Preparation of metallic bismuth nanoparticles and nanocrystalline bulk dismuth metal", Journal of Nanoparticle Research, 2006, pp. 729-736.
Waltimo et al., "Antimicrobial Effect of Nanometric Bioactive Glass 45S5", Research Reports, Biomaterials & Bioengineering, J Dent Res 86(8), 2007, pp. 754-757.
Gubler et al., "Do bioactive glasses convey a disinfecting mechanism beyond a mere increase in pH?", International Endodontic Journal, 41, 2008, pp. 670-678.
Vollenweider et al., "Remineralization of human dentin using ultrafine bioactive glass particles", Acta Biomaterialia 3, 2007, pp. 936-943.

* cited by examiner

*Primary Examiner* — Robert A Wax
*Assistant Examiner* — Danah Al-Awadi
(74) *Attorney, Agent, or Firm* — Renner, Otto, Boisselle & Sklar, LLP

(57) ABSTRACT

Nanoparticulate material containing a matrix and embedded therein a radiopacifier are bioactive, show a high alkaline capacity and are radio-opaque. Compositions and formulations including such material are particularly useful in advanced dental applications, such as dental fillings and/or disinfection.

24 Claims, 3 Drawing Sheets

RADIO-OPAQUE BIOACTIVE GLASS MATERIALS

This application is a national phase of International Application No. PCT/CH2010/000200 filed Aug. 17, 2010, and published in the English language which claims priority to EP 09010656.8 filed Aug. 19, 2009.

The invention relates to a nanoparticulate material containing a matrix and embedded therein a radiopacifier; to compositions and formulations comprising (i.e. containing or consisting of) such material. The invention further relates to the manufacturing of such materials, compositions and formulations and to uses thereof, particularly in advanced dental applications, such as root canal fillings and/or disinfection. Particularly, the present invention describes materials which are bioactive, show a high alkaline capacity and are radio-opaque.

Bioactive glass ("BG") is a known material which is not radio-opaque. Therefore, it was suggested to combine such material with a radiopacifier to identify it on a radio-graphic image, see e.g. Madanat et al Acta Biomater. 2009, 5(9), 3497-505. In this document, it is suggested to combine particles of bioactive glass with particles of BaSO4, melting the mixture to obtain shaped implants. However, it was found that the materials produced according to this method show reduced bioactivity.

Nanoparticulate bismuth and bismuth oxide are known, see e.g. Grass et al., 2006, J. Nanopart. Res., 8, 729-36. Such materials may be used in thermoelectric applications, but are considered unsuitable for direct use in dental applications.

Further, various documents disclose nanoparticulate materials, but are silent about radiopacifiers or X-ray properties. For example, WO2008/049242 discloses amorphous tricalciumphosphate nanoparticles and speculates about doping said particles with silver. Brunner et al (Chem Comm 2006, 1384) discloses bioglass nanoparticles doped with cobalt or gold.

Thus, it is an object of the present invention to mitigate at least some of these drawbacks of the state of the art. In particular, it is an aim of the present invention to provide materials which are suitable for advanced dental applications, such as root canal filling and/or disinfection, overcoming the disadvantages of the prior art.

The present invention will be described in more detail below. It is understood that the various embodiments, preferences and ranges as provided/disclosed in this specification may be combined at will. Further, depending of the specific embodiment, selected definitions, embodiments or ranges may not apply. It is further understood that all references identified herein are incorporated by reference in its entirety.

The above objectives are achieved by providing a particle as defined in claim 1. Further aspects of the invention are disclosed in the specification and independent claims, preferred embodiments are disclosed in the specification and the dependent claims. Particles as described herein prove to be useful in dental applications as defined below and further provide new and useful formulations, as defined below.

As it will become apparent when reading this specification, the invention relates in a first aspect to (uncoated) nanoparticles/compositions of the bioactive glass-type which are radio-opaque and the manufacturing thereof; in a second aspect to coated nanoparticles/compositions of the bioactive glass-type which are radio-opaque and the manufacturing thereof; in a third aspect to formulations comprising such nanoparticles and the manufacturing thereof; in a fourth aspect to uses of such nanoparticles/compositions and formulations.

The invention will be better understood and objects other than those set forth above will become apparent when consideration is given to the following detailed description thereof.

Further, the present invention will be better understood by reference to the figures.

Figure 3:
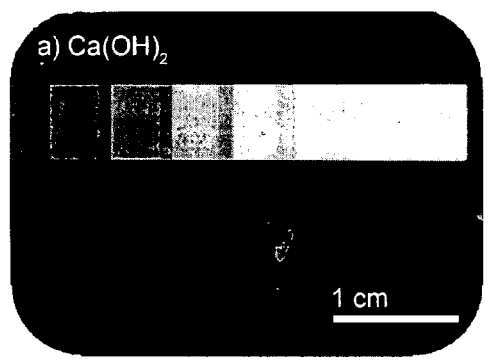
Figure 3:
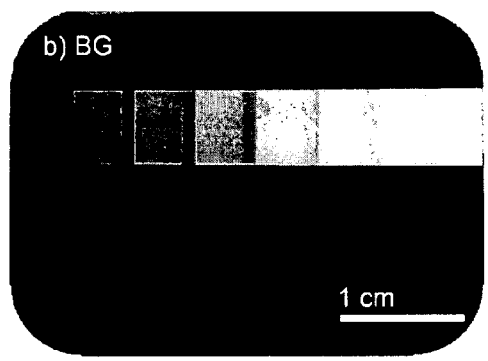
Figure 3:
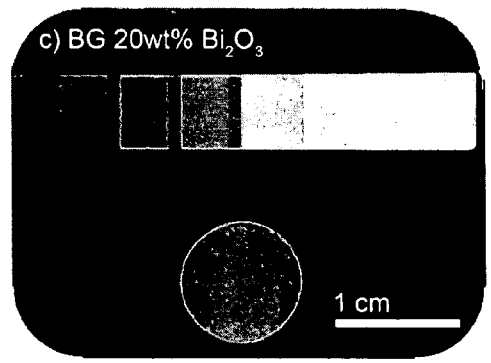
Figure 3:
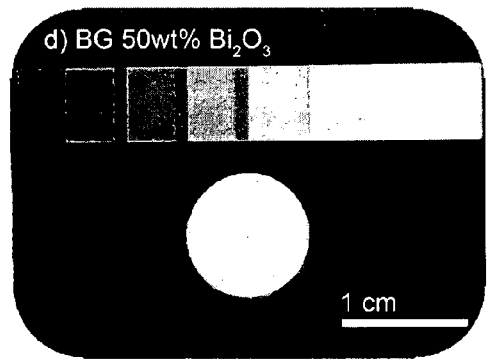

FIG. 3 shows radiographic images of bioactive particles (flame derived), reference material and an aluminum step wedge, wherein: (a) calcium hydroxide as reference material for root canal disinfection; (b) bioactive particles according to the prior art (BG45S5); (c) bioactive particles with 20 wt % bismuth oxide, according to the invention; (d) bioactive particles with 50 wt % bismuth oxide, according to the invention. As can be seen, a significant radiopacity can be obtained with 20 wt % bismuth oxide.

Figure 4:
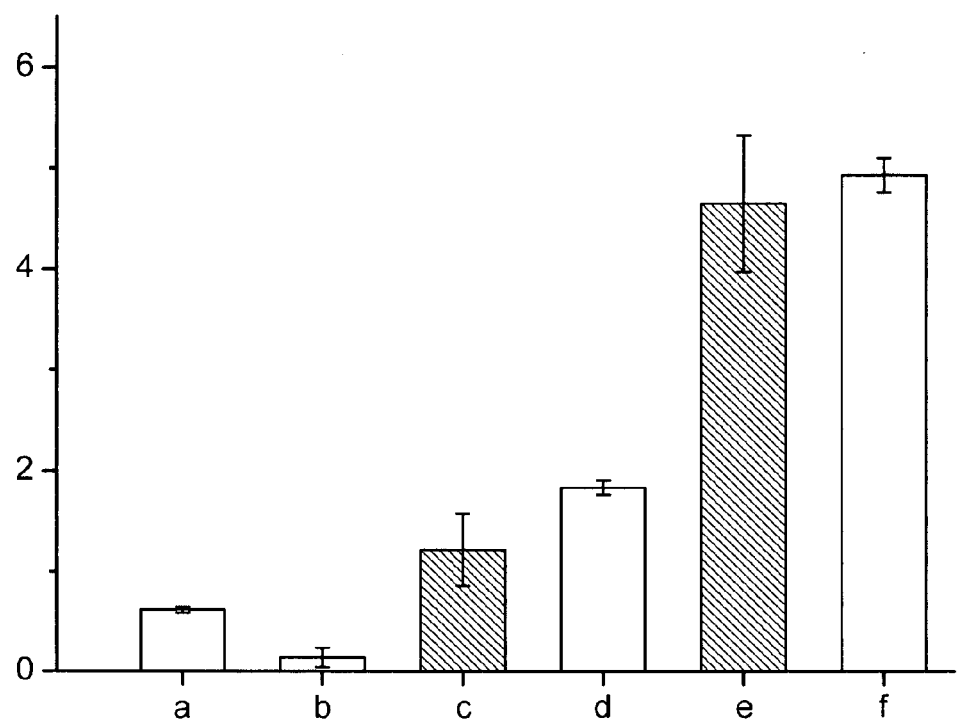

FIG. 4 shows the relative radiopacity of tested materials in comparison with an aluminum step wedge showing the mean and the standard deviation (n=3) in mm aluminum equivalents (y-axis). The letters from a-f denote the tested materials on the x-axis, whereas the dashed bars indicate mechanical mixtures: (a) bovine dentine; (b) bioactive particles, according to the prior art; (c) mechanical mixture of bioactive particles with 20 wt % bismuth oxide, according to the prior art; (d) flame derived bioactive particles with 20 wt % bismuth oxide, according to the invention (manufactured as outlined in example 2); (e) mechanical mixture of bioactive particles with 50 wt % bismuth oxide, according to the prior art; (f) flame derived bioactive particles with 50 wt % bismuth oxide, according to the invention (manufactured as outlined in example 3). As can be seen, an improved radiopacity and a reduced standard deviation are obtained when comparing the inventive particles with mixtures of known particles.

Figure 5:
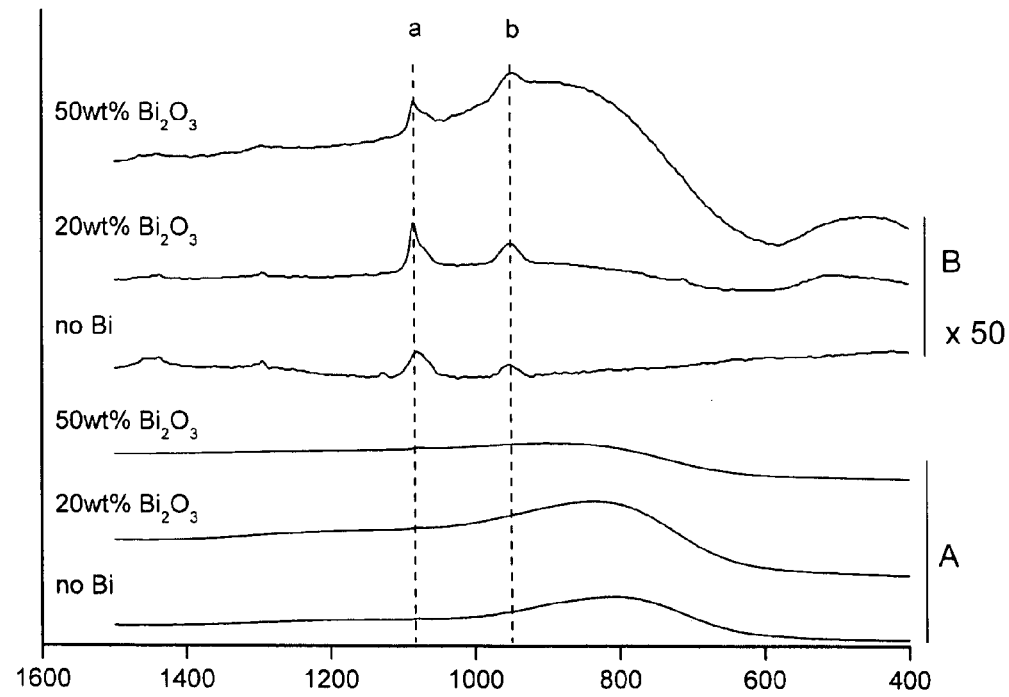

FIG. 5 shows Raman spectroscopy of as prepared (flame derived) bioactive particles (A) and after immersion in simulated body fluid (SBF) up to 7 days (B) showing the formation of carbonated hydroxyapatite. The peak (a) at 1070 cm-1 indicates the presence of carbonate; the peak (b) at 960 cm-1 indicates the presence of hydroxyapatite. The y-axis gives the intensity in arbitrary units and the x-axis is the wavelength in cm-1. The data clearly show that the inventive particles are bioactive.

Figure 6:
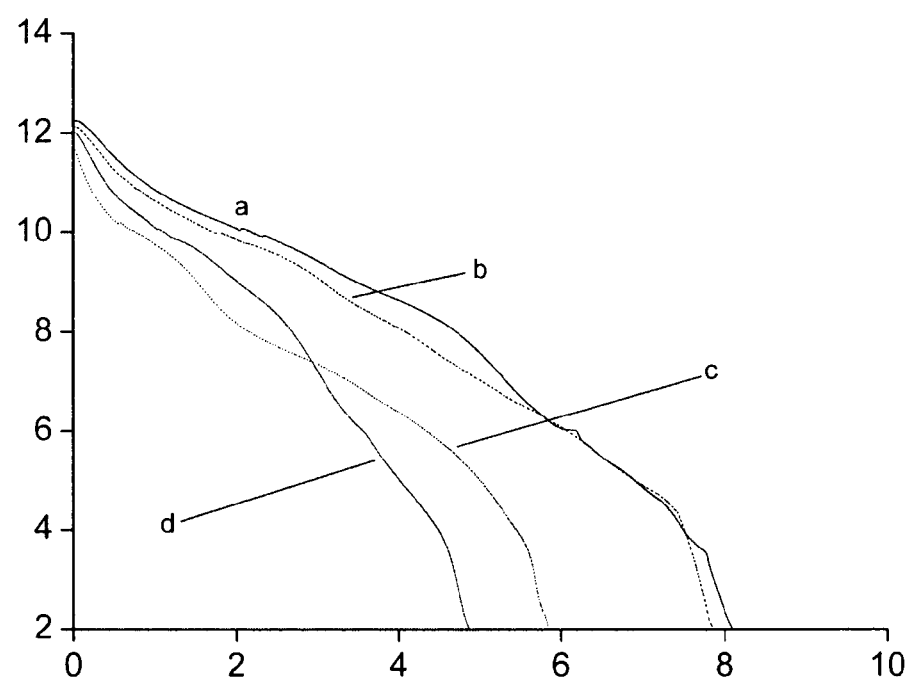

FIG. 6 shows a continuous titration of bioactive particle suspensions with 1M HCl and a constant flow rate of 1.78 ml per hour. The y-axis depicts the pH and the x-axis gives the time in hours. The letters denote the following materials: (a) bioactive particles, according to the prior art; (b) flame derived bioactive particles with 20 wt % bismuth oxide, according to this invention (manufactured as outlined in example 2); (c) flame derived bioactive particles with 50 wt % bismuth oxide, according to this invention (manufactured as described in example 3); (d) mechanical mixture of bioactive particles with 50 wt % bismuth oxide, according to the prior art. The figure reveals that bismuth oxide doping of bioactive particles has only little influence on the alkaline power, particularly when compared to a mechanical mixture of the components.

Unless otherwise stated, the following definitions shall apply in this specification:

The "diameter" of a particle as described herein is the volume-surface-average diameter of the primary particle.

This may be determined by nitrogen adsorption using the BET method (according to: Janssen et al, *Journal of Applied Polymer Science* 52, 1913, 1994).

The term "Radio-opacity" (or "radiopacity") is known in the field and described e.g. in EN ISO6876. Briefly, the term refers to the relative inability of electromagnetism, such as X-rays, to pass through a given material. Dense materials which prevent the passage of electromagnetic radiation, such as X-rays, are called 'radio-opaque'. Thus, the term refers to the relative opaque white appearance in radio-graphic imaging, when passing electromagnetic radiation, such as X-rays, through dense matter.

The term "Bioactivity" or "bioactive material" is known in the field. Briefly, the term refers to the ability of a material to induce calcium phosphate deposition on the surface of the object when placed in fluids. These fluids can be but are not limited to simulated body fluid, phosphate buffered or unbuffered physiological sodium chloride solution and the fluid in a living organism.

The term "Biodegradation" or "biodegradability" is known in the field. Briefly, the term is used herein to relate the degradation of materials by humidified atmospheres and/or by liquid at various temperatures and/or cellular action. The characteristic parameter for the degradation is the mass loss of the material and/or the reduction in molecular weight of the applied material.

In general terms, the present invention relates in a first aspect to specific nanoparticles of the bioactive glass type as outlined below.

In one embodiment, the invention relates to Primary Particles with a diameter below 200 nm containing a matrix and embedded therein a radiopacifier, wherein said matrix contains oxides of Si, Ca, Na and optionally P and wherein said radiopacifier is selected from the group consisting of metals, metal oxides and metal salts (such as phosphates, halogenides, sulphates), preferably metals and metal oxides, of elements with an atomic mass greater than 20, preferably greater than 85. Elements with an atomic mass greater than 20 include the elements starting from the $3^{rd}$ period; those with an atomic mass greater than 85 include the elements starting from the $5^{th}$ period of the periodic table. Such nanoparticles prove to be bioactive, are radio-opaque and show a high degree of alkaline capacity.

This aspect of the invention shall be explained in further detail below.

Primary Particle:

The invention relates to particles in the nanometer scale, such particles are often termed "nanoparticles". Suitable are particles between 20-200 nm, preferably 20-50 nm, particularly preferably 20-100 nm. Such particle size results in material having a high surface area (e.g. >30 m²/g). This allows a homogeneous distribution in a formulation as defined below and improved quality during X-ray investigations. Nanoparticles, in the context of this invention, comprise primary particles and secondary particles. The term secondary particle includes such particles which are formed by interaction of primary particles. These secondary particles can be significantly larger than primary particles. Secondary particles can be formed by primary particles attached to each-other by physical forces, such as Van-der-Waals forces, or by individual primary particles grown together which have solid necks between the individual primary particles and can be formed by Oswald ripening or sintering. The 3-D fractal dimension of the secondary particles can vary over a wide range from just above 1 to nearly 3.

Matrix:

As outlined above, the matrix of the inventive particles contains (or consists of) oxides of Si, Ca, Na and optionally P. Advantageously, the matrix is of the bioactive glass type. Suitable bioactive glasses comprise a matrix of silicon oxide and additional metal oxides. Examples of additional oxides include but are not limited to sodium oxide, calcium oxide, phosphorous oxide, aluminum oxide, boron oxide, strontium oxide, potassium oxide, magnesium oxide or combinations and mixtures thereof. Preferably, a bioactive glass suitable as matrix for the inventive particles contains calcium oxide, sodium oxide and phosphorous oxide as additional oxide. The matrix typically contains $SiO_2$ in an amount of less than 66 wt %, such as 20-60 wt %, preferably 30-50 wt %. The matrix typically contains CaO in an amount of 10-50 wt %, preferably 20-40 wt %. The matrix typically contains $Na_2O$ in an amount of 5-50 wt %, preferably 15-30 wt %. The matrix typically contains $P_2O_5$ in an amount of 0-20 wt %, preferably 3-10 wt %. It is believed that $P_2O_5$ supports nucleation of calcium phosphate, which deposits on the surface; it is not considered essential. Bioactive glasses distinguish from calciumphosphates in that (i) silica is present, (ii) the amount of sodium is higher (aqueous solutions thereof show a high ph value) and (iii) phosphorous is an optional component.

Radiopacifier:

As outlined above, the inventive particle contains in addition to the matrix one or more radiopacifiers. In general, any inorganic radiopacifier may be used in the context of the present invention.

Typically, radiopacifiers are selected from the group consisting of metals, metal oxides or metal salts of tungsten, tantalum, silver, bismuth, holmium, niobium, iron, titanium, barium, aluminum and strontium, such as barium sulphate, silver oxide, bismuth oxide, bismuth carbonate, bismuth nitrate, calcium tungstate, tantalum oxide. Preferably, radio-opaque agents are selected from the group consisting of tungsten (preferentially W), tantalum (preferentially $TaO_2$ or $Ta_2O_5$), silver (preferentially Ag or AgO), bismuth (preferentially $Bi_2O_3$), holmium (preferentially Ho or $Ho_2O_3$), Niobium (preferentially $Nb_2O_5$), iron (preferentially Fe or FeO or $Fe_2O_3$ or $Fe_3O_4$), titanium (preferentially Ti or $TiO_2$), barium (preferentially BaO or $BaSO_4$), aluminium (preferentially $Al_2O_3$) strontium (preferentially SrO).

In a further embodiment, radiopacifiers are selected from the group consisting of metals, metal oxides or metal salts of rubidium, strontium, yttrium, zirconium, niobium, molybdenum, tin, caesium, barium, lanthanum, hafnium, tantalum, tungsten, bismuth and rare earth elements; such as barium sulphate, bismuth oxide, bismuth carbonate, bismuth nitrate, calcium tungstate, tantalum oxide. Preferably, radiopacifiers are selected from the group consisting of tungsten (preferentially $WO_3$), tantalum (preferentially $TaO_2$ or $Ta_2O_5$), bismuth (preferentially $Bi_2O_3$), holmium (preferentially $Ho_2O_3$), Niobium (preferentially $Nb_2O_5$), barium (preferentially BaO or $BaSO_4$), rubidium (preferentially $RbO_2$), yttrium (preferentially $Y_2O_3$), zirconium (preferentially $ZrO_2$), caesium (preferentially $CsO_2$), ytterbium (preferentially $Yb_2O_3$ or $YbF_3$), cerium (preferentially $CeO_2$), molybdenum (preferentially $MoO_3$), tin (preferentially SnO or $SnO_2$), hafnium (preferentially HfO), lanthanum (preferentially $La_2O_3$) and strontium (preferentially SrO) and optionally zinc (preferentially ZnO).

In a still further embodiment, the radiopacifier is selected from the group consisting of $Bi_2O_3$, $TaO_2$, $Ta_2O_5$, $WO_3$, BaO.

In a still further embodiment, the radiopacifier is $Bi_2O_3$. It is understood that the inorganic radiopacifier may be present in any stable oxidation state, depending on the specific material, this may be +/−0, +I, +II ... up to +VII. It is believed that the small particle size (nano-scale) of the inventive particle influences stability of the inorganic radiopacifier. The invention thus includes metals, metal oxides and other metal salts present in the inventive particles as radiopacifier. The radiopacifier is distributed in and/or on the matrix, typically homogeneously distributed. Thus, the invention relates in an advantageous embodiment to particles, wherein radiopacifier and matrix as defined herein are present as separate phases; the matrix forms a support for the radiopacifier.

The amount of radiopacifier may be varied in a broad range, and may be determined by routine experiments. For the uses as outlined below, an effective amount of radiopacifier is to be included in the primary particle; typically, such amount is 50 wt % or less of the primary particle. Suitable are, for example 5-50 wt %, even an amount as low as 25-40 wt % provides a high degree of radiopacity. It was surprisingly found that mixing mechanically 50 wt % of a radiopacifier (such as barium sulphate) into bioactive glass shows less radiopacity than adding 50 wt % of bismuth oxide by the flame spray synthesis. Further, the homogeneity is improved, as the lower standard deviation shows, see FIG. 4. Thus, the present invention provides a method of reducing the amount of radiopacifier by maintaining the radiopacity.

In an advantageous embodiment of the present invention, the ratio Ca:P in the inventive particle is in the range of 10:1 to 1:10.

In an advantageous embodiment of the present invention, the ratio Ca:Na is in the range of 2:1 to 0.5:1.

In a further embodiment, the invention relates to a composition containing a plurality of particles as described herein. Such material is advantageously produced by flame spray synthesis as described below. It is a material with low-density and snow-like behaviour. Advantageously, this material is compacted prior to further processing. Suitable compaction methods are known in the field and include grinding, pressing (preferentially uniaxial pressing) and/or by a dual asymmetric centrifuge. In one embodiment, an uniaxial pressure of about 2.6 MPa is applied to obtain a suitable composition. It was surprisingly found that such compacting does not affect the structure of the particles of the invention, i.e. the particles are stable and particularly do not sinter. Such measure improves handling and particularly enables a high loading of particles into a formulation (mass particles per volume formulation) as described below. The bulk density of the composition (mass of the composition divided by its volume) is advantageously in the range of 0.2-1.5 g cm-3, preferably 0.3-0.7 g cm-3. Consequently, the invention also relates to a composition having a bulk density above 0.2 g cm-3 (preferably above 0.3 g cm-3), and consisting of one or more types of particles as disclosed herein.

In a further embodiment, one or more types of other particles, typically also in the nanometer scale as defined herein, may be combined with the inventive particles. The amount of such particles may be up to 50 wt %, preferably up to 5 wt %. Consequently, the invention relates to a composition as disclosed herein, consisting of particles as disclosed herein and optionally up to 50 wt % of further nanoparticles. Such "other particles" may be selected from the radiopacifiers identified above and further include $BaSO_4$ and $Bi_2O_3$, preferably $BaSO_4$. In a preferred embodiment, the inventive particles are combined with ZnO.

In a further embodiment, the invention relates to particles/compositions as disclosed herein that are bioactive. The term "bioactive" particularly refers to the ability of these particles/compositions to bond bone and/or soft tissue. Without being bound to theory, it is believed that via corrosion in a liquid environment with continuous replenishment of the liquid phase, bioactive glass particles undergo a multi-step alteration, which results in a Ca—P rich layer on the glass surface which may lead to partial or complete replacement of the glass by hard tissue. Such transformation and the resulting release of glass components into solution are influenced inter alia by glass composition and per-weight surface area. Standard bioactive glass compositions exhibit a carbonated hydroxyapatite layer upon immersion in simulated body fluid or physiological sodium chloride solution. Applying the inventive radio-opaque bioactive glass particles to the same procedure also results in a carbonated hydroxyapatite layer, which can be analyzed by Raman spectroscopy (FIG. 5), or other methods such as scanning electron microscopy or X-ray diffraction. This proofs the bioactivity of the here described particles. Consequently, the particles as described herein may be also described as bioactive glass with a particle size in the nanometer range. Consequently, the invention provides particles/compositions that belong to the group of bioactive glasses ("BG").

In a further embodiment, the invention relates to particles/compositions as disclosed herein having a narrow particle size distribution. The distribution of the particle diameter is evaluated by measuring the particle diameters of at least 200 individual, representative particles from transmission electron micrographs. The particle size distribution is then fitted by a log-normal distribution (see Grass and Stark, Journal of Materials Chemistry 2006 Vol. 16, P 1825 ff). The distribution is characterized as narrow if the geometric standard deviation of the measured and fitted distribution is below 1.9, more preferably below 1.7 and most preferably below 1.5. A narrow size distribution, as described above, improves the quality of the material and simplifies the uses disclosed herein.

In a further embodiment, the invention relates to particles/compositions as disclosed herein having high alkaline capacity. It is known that bioactive glass is useful for the reduction of oral microorganisms; it is believed that this effect is induced by the alkaline environment and by the ion release of a bioactive glass. By the direct incorporation of the radiopacifier, the alkalinity of the material is not reduced by the same extent, i.e. addition of 50% does not reduce the alkaline power by half in comparison to a mere mechanical mixture (FIG. 6). This demonstrates that the inventive particles/compositions afford a higher alkalinity than a physical mixture (by milling together the constituents) of bioactive glass and a radiopacifier.

In a further embodiment, the invention relates to a method of manufacturing particles as described herein comprising the step of subjecting one or more combustible solutions to a flame spray pyrolysis wherein said one or more solutions contain one or more soluble silica precursors, such as hexamethyldisiloxane, tetraethoxysilane or any other organosilicon compounds;

one or more soluble sodium precursors, such as sodium 2-ethylhexanoate or any kind of soluble sodium source such as sodium carboxylate;

one or more soluble calcium precursors, such as calcium 2-ethylhexanoate or any kind of soluble calcium source such as calcium carboxylate;

optionally one or more soluble phosphorous precursors, such as tributyl phosphate or any other soluble phosphorous source such as organophosphorous compounds;

one or more soluble precursors of a metal having an atomic mass above 20 (preferably above 85), such as soluble precursors selected from the group consisting of tungsten, tantalum, bismuth, holmium, niobium, barium, rubidium, yttrium, cesium, cerium, ytterbium, tin and strontium. Suitable precursors of a metal having an atomic mass above 20 include tantalum ethoxide, tantalum butoxide, tantalum methoxide, bismuth 2-ethylhexanoate, holmium isopropoxide, niobium 2-ethylhexanoate, niobium n-butoxide, barium 2-ethylhexanoate, rubidium 2-ethylhexoxide, yttrium 2-ethylhexanoate, cesium 2-ethylhexoxide, cerium 2-ethylhexanoate, ytterbium isopropoxide, ytterbium 2-ethylhexanote or strontium 2-ethylhexanoate.

Such FSP processes are known per se, but not applied to the present combination of starting materials. The process may be performed as described in WO 2005/087660 by adding one or more extra precursor containing at least one heavier element at which the corresponding oxide is heavier than calcium oxide. It is understood that the element mass ratio of original bioactive glass compositions, for example Bioglass 45S5® (45 wt % SiO2, 24.5 wt % CaO, 24.5 wt % Na2O, 6 wt % P2O5) are kept constant although one or more metal oxides are added. The supplementary metal oxides, which introduce the radiopacity, do not substitute one of the original metal oxides, which are necessary for bioactive glasses. A suitable composition according to this invention is, 22.5 wt % SiO2, 12.25 wt % CaO, 12.25 wt % Na2O, 3 wt % P2O5, 50 wt % Bi2O3.

In a further embodiment, the invention relates to a method of manufacturing a composition as described herein comprising the step of a) providing one or more types of particles as described herein and optionally one or more further nanoparticles, b) densifying these particles to obtain a composition having a bulk density of at least 0.3 g*cm$^{-3}$.

In a further embodiment, the invention relate to particles and compositions as disclosed herein that are obtainable by or obtained by a FSP process, particularly by a FSP process as disclosed herein.

The present invention relates in a second aspect to particles as disclosed herein further comprising a surface functionalization and/or their linkage to other molecules. Such functionalization may improve dispersing properties of the inventive particles.

This aspect of the invention shall be explained in further detail below:

In one embodiment, the invention relates to a coated particle containing one or more particles as described above (1$^{st}$ aspect of the invention), additionally containing a coating. Such particles may be considered as being of the "core-shell-type", the core being formed of a primary particle as disclosed above, the shell being formed of a coating as described below. The term coated particles further includes such particles wherein a multitude of uncoated particles is coated with a coating as described below. Thus, the term coated particles covers one or more primary and/or secondary particles coated with a coating as defined below. It is further understood that the term particle excludes fibrous materials. Particles may have similar aspect ratios, may be in the form of needles or plates; preferably having a circle and/or sphere shaped form if analyzed by visualizable techniques (such as electron scanning microscopy).

A wide variety of coatings, particularly pharmaceutically acceptable coatings, may be applied to the particles as disclosed herein. Such coating may cover the inventive particles partly or fully. Further, such coating may be bound to the inventive particles covalently or by intermolecular forces (e.g. adsorption of a detergent or wetting agent). The coating may consist of a) functionalized molecules with a molecular mass below 2000 g/mol and/or b) polymers with a molecular mass above 2000 g/mol.

Suitable functionalized molecules include small molecules with one or more functional groups, surfactants, wetting agents. Small molecules include compounds having a molecular weight below 2000 g/mol, preferably 500 g/mol. Typically, small molecules are bound covalently to the surface of the inventive particles.

Suitable small molecules include functionalized alkylsilanes (such as 3-aminopropyl-triethoxysilane and/or triethoxy (1H,1H,2H,2H-perfluoro 1-octyl)silane). It was found that coating the inventive particles/composites with the above fluorosilane provides good results when combined with fluorinated polymers.

Suitable surfactants include Polysorbat 20 (Tween 20®), Polysorbat 80 (Tween 80), Pullulan, Sodium dodecyl sulphate (SDS). It was found that coating the inventive particles/composites with the above surfactants provides good results in dental applications when combined with silicon containing polymers.

Suitable wetting agents are known in the field and include the compounds identified above as "surfactants". It was found that coating the inventive particles/composites with the above wetting agents provides good dispersability of the inventive particles/composites in dental applications. It is known in the field that many surfactants also have properties as wetting agents and vice versa. Thus, one component may fulfil both requirements, as wetting agent and surfactant; alternatively, two or more components may be included to specifically meet all requirements.

Suitable polymers include compounds having a molecular weight in the range of 2'000-100'000 g/mol. Examples for such polymers are poly-ethylen-glycoles or poly-urethanes. Typically, such polymers are bound by intermolecular forces, such as adsorption, to the surface of the inventive material. The polymers identified above may be crosslinked prior to application. It was found that coating the inventive particles/composites with the above polymers provides good results in terms of incorporation into the backbone of a polymer and/or into the polymeric matrix for dental applications.

In a further embodiment, the invention relates to a composition containing a plurality of particles having a surface functionalization and/or linkage to other molecules as described herein. Suitable densities of such compositions correspond to the values given above (1$^{st}$ aspect), as well as manufacturing methods and combinations with other nanoparticles.

The present invention relates in a third aspect to formulations comprising particles/compositions according to the first or second aspect of the invention and one or more excipients. The inventive formulations combine bioactive properties, radio-opaque properties and high alkaline capacity.

This aspect of the invention shall be explained in further detail below:

Contrary to the prior art, the inventive formulations by itself are radio-opaque and do not require admixing of additional radiopacifiers. This therefore saves one step in the manufacturing process and further improves quality of the formulations, particularly homogeneity of the material. This helps the dentist to monitor their placement radio-graphically more precisely.

As outlined above, the invention relates to an improved bioactive glass formulation which is useful in dental applications. The inventive formulations additionally show high alkaline capacity, particularly when compared to radio-opaque formulations of the prior art. This improves the antimicrobial effect of bioactive glass formulation. Typically, the pH of the inventive formulations, particularly the liquid formulations, is equal to or greater than 11.

Suitable excipients are those known in the field, and may be selected according to the intended use. It was found that the inventive particles/compositions are compatible with the excipients used in the field. The amount of excipients in an inventive formulation may vary over a broad range; typically the amount of excipients in a formulation is in the range of 10-90 wt %, typically 20-80 wt %. Correspondingly, the amount of particles/compositions is in the range of 90-10 wt %, preferably 80-20 wt %.

Suspensions:

In one embodiment, the invention relates to a formulation as defined above, wherein said excipients are selected from the group consisting of aqueous solutions. A wide variety of aqueous solutions may be combined with the inventive particles/compositions. Preferably, pharmaceutically acceptable solutions, such as water (including distilled water, ultrapure water), physiologically acceptable saline solutions, synthetic body fluid, ringer solution, or other physiologically acceptable antiseptic solutions (including aqueous sodium hypochlorite solutions and aqueous chlorhexidine solutions); preferably physiological sodium chloride solution or sodium hypochlorite and more preferably sodium hypochlorite solutions are used. Such aqueous solutions are known in the field. Applying a mere powder (i.e. particles or compositions as disclosed herein) in a root canal or other dental cavity is considered not convenient in practice, as a lentulo spiral or other rotating instrument is typically used. Typically, formulations in form of a paste or suspension are used. Such formulations are obtainable by combining the inventive particles/compositions with one or more aqueous solutions, in an amount to obtain an aqueous formulation showing the required rheological properties.

In an advantageous embodiment, the invention provides a formulation containing (i.e. comprising or consisting of) (i) particles with a diameter below 200 nm as described herein ($1^{st}$ aspect of the invention), (ii) an aqueous solution. Component (i) may be present in amount from 10-wt %, preferably 35-55 wt %; component (ii) may be present in an amount from 40-90, preferably 45-65 wt %.

Polymers:

In a further embodiment, the invention relates to a formulation as defined above, wherein said excipients are selected from the group consisting of polymers. A wide variety of polymers may be combined with the inventive particles/compositions. Preferably, pharmaceutically acceptable polymers, such as biodegradable and non-biodegradable polymers are used. Such polymers are known in the field. Suitable polymers include thermoplastic polymers (such as the biodegradable polymers identified below) or elastomeric polymers (such as polyisoprenes identified below).

Suitable biodegradable polymers may be selected from the group consisting of poly-lactides, poly-glycolides, polycaprolactones, polyalkanoates (preferably polyhydroxybutyrates, polyhydroxyvalerates, polyhydroxyhexanoates, polyhydroxyoctanoates), polypropylene fumarates, chitin, chitosan, and combinations (copolymers or blends) thereof. Such formulations are particularly suitable for application as root canal sealer. Suitable non-biodegradable polymers may be selected from the group consisting of polyisoprenes (PIP) and combinations of polyisoprenes with other polymers. Further, suitable non-biodegradable polymers may be selected from the group consisting of polyacrylates and/or poly-methacrylates. Such formulations are particularly suitable for manufacturing of a pin and/or post in dental applications.

In an advantageous embodiment, the invention provides a formulation containing (i.e. comprising or consisting of) (i) particles with a diameter below 200 nm as described herein ($1^{st}$ aspect of the invention), (ii) ZnO particles with a diameter below 200 nm, and (iii) one or more polymers as described herein (preferably non-biodegradable polymers such as PIP). Component (i) may be present in amount from 10-40 wt %, preferably 15-35 wt %; component (ii) may be present in an amount from 40-80, preferably 45-65 wt %; component (iii) may be present in an amount from 20-40 wt %, preferably 25-35 wt %. Such formulations show advantageous properties with regards to radiopacity and simultaneously with regards to plasticity and usability.

In a further advantageous embodiment, the invention provides a formulation containing components (i) (ii) and (iii) as defined above, being free from sealing materials. Conventional formulations in the field of dental surgery include sealing materials ("sealers"), typically selected from the group consisting of epoxy resins and silicon based materials. It was surprisingly found that such sealers are not required when using the inventive formulations. Thus, the invention also provides formulations free of, or essentially free of, sealers.

Manufacturing:

In a further embodiment, the invention relates to a method of manufacturing a formulation as described herein comprising the step of combining primary particles or compositions as described in the first or second aspect of the invention with one or more excipients.

The present invention relates in a fourth aspect to uses/methods of use of the compositions and formulations as disclosed herein. In general, the inventive compositions and formulations retain the beneficial properties of bioactive glass materials and are thus suitable for all uses that are applicable to known bioactive material; this particularly includes the uses as disclosed herein.

In one embodiment, the present invention relates to a formulation as disclosed herein as pharmaceutical/for use as pharmaceutical.

In a further embodiment, the present invention relates to a formulation as disclosed herein for use in the treatment of dental diseases/for use in the manufacturing of a medicament for the treatment of dental diseases. Consequently, the invention also provides a method of treatment of a dental disease comprising the step of administering/applying an effective amount of a formulation as disclosed to a subject in need thereof. The term dental disease is known in the field and particularly relates to the use as disinfectant (particularly for use in dentine, root canal, and periodontal disinfection) or to the use as filling material (particularly for use as endodontic filling material or periodontal grafting material).

The present invention provides a formulation which is ideally tailored, and thus useful, for the treatment of infected root canal systems and decayed dentine.

The present invention provides a formulation comprising a radio-opaque bioactive glass and a liquid and/or a biodegradable polymer and/or a non-biodegradable polymer which forms a filling material. The inventive formulations may be used as a topical disinfectant, intermediate root canal dressing, root canal filling and re-mineralization agent. In contrast to existing formulations, the present material combines all desired properties; i.e. radio-opacity, antimicrobial action, bioactivity, high alkaline capacity, ease of application.

The present invention provides a formulation which is ideally tailored, and thus useful, i) as alloplastic bone grafting material; ii) for the treatment of extraction sockets, particularly to reduce postoperative pain and to prevented localized osteitis; iii) for disinfecting and/or remineralizing decayed dentine; iv) as a component in dentifrices, particularly to reduce plaque formation and gingival bleeding; and/or v) as a root canal disinfectant.

To further illustrate the invention, the following examples are provided. These examples are provided with no intend to limit the scope of the invention Preparation and Characterization of Radio-Opaque Bioactive Particles:

Nanosized bioactive particles were produced in a flame spray setup. Corresponding amounts of calcium 2-ethylhexanoate and sodium 2-ethylhexanoate were mixed with hexamethyldisiloxane and tributyl phosphate and diluted with xylene. This solution was subsequently filtrated. The solution was pumped (5 ml min-1) through a capillary with a diameter of 0.4 mm. The solution was dispersed with oxygen (5 l min-1) and ignited with a methane/oxygen flame with a gas-flowrate of 1.13 l min-1 and 2.4 l min-1, respectively. The as-formed bioactive nanoparticles were collected on a fibre filter (25.7 cm diameter) with the aid of a vacuum pump (For detailed examples see below). To introduce radiopacity, an organic bismuth precursor {Grass et al., 2006, J. Nanopart. Res., 8, 729-36} was added to the starting material and yielded bioactive nanoparticles with 20 wt % and 50 wt % of bismuth oxide. The ratios of all constituents of classical bioactive particles in the radio-opaque bioactive particles were kept constant. Calcium hydroxide (puriss.) from Riedel-de Haen (Germany) was used as gold standard for root canal disinfection. Bismuth oxide (purum) and barium sulphate (purum) as commercially available radiopacifier were procured from Fluka (Switzerland). The specific surface area (SSA) of the as prepared nanomaterials was measured on a Micromeritics Tristar (Gosford, NSW, Australia) by nitrogen adsorption at 77 K using the Brunauer-Emmet-Teller (BET) method after outgasing for 1 hour at 150° C. A transmission electron microscope (CM30 ST, LaB6 cathode, Philips Electron Optics, The Netherlands) operated at 300 kV at a point resolution 0.4 nm was used to study the morphology and to confirm the particle size.

Radiopacity Assessment:

According to Waltimo et al., 2009, J Dent Res, 88, 235-8, the amount of bioactive particles per volume plays an important role in the closed environment of a root canal. To achieve a denser packing of the naturally relatively light nanomaterial (low-density powder with snow-like behaviour), uniaxial pressure of 2.6 MPa was applied for 30 seconds. Grinding of the densified material subsequently resulted in a smooth and dense powder. The thus improved filler was compared to classical (flame derived) bioactive particles (no bismuth), to mechanical mixtures of bioactive particles and barium sulphate (50/wt %) and bismuth oxide (80/20 wt %; 50/50 wt %). Calcium hydroxide with or without additional barium sulphate was used as commercially available control material. Bovine dentine slices with a thickness of 1 mm served as control for the clear distinction between material and the surrounding tissue in clinical situations. Prior to use, the corresponding powder was homogeneously mixed with unbuffered physiological saline (0.9 wt % NaCl) to obtain a final weight to volume ratio of 60% (plastic limit, i.e. the maximum amount of powder per liquid to yield a paste-like suspension). A radiograph was taken after preparing the paste and placing it in a polycarbonate mould (10 mm diameter, 1 mm thick). Specimens were placed on a radio-graphic film (Digora, Finland) together with an aluminum step-wedge with a variable thickness from 0.5 mm to 6 mm (0.5 mm and 1 mm increments). A Trophy Irix (Trophy, Paris, France) X-ray unit operating at 65 kV, 8 mA and 0.22 s with a focus-film distance of 25 cm was used. The paste-samples were prepared immediately prior to use in the X-ray unit and radiographic analysis was done in triplicates. Digital radiographic images were imported with a Digora system (Soredex, Finland), using Digora software for Windows without grey scale correction. Optimas imaging analysis software (Meyer Instruments Inc., Houston, Tex., USA) was used to determine the mean gray value of the samples and convert the mean gray value to millimeters of aluminum equivalent.

In Vitro Bioactivity:

The bioactivity of the novel derived bioactive nanoparticles incorporating bismuth oxide was tested using simulated body fluid (SBF) {Kokubo et al., 1990, J. Biomed. Mater. Res. 24, 721-734}. Pressed bioactive particles were placed up to 7 days in SBF at 37° C. {Brunner et al., 2006, Chem. Commun, 1384-6}. Raman spectra (EQUINOX 55 and FRA 160/S Bruker optics, Germany) were recorded in backscattering mode {Notingher et al., 2002, Mater. Charact., 49, 255-60}. Surface examination of bioactive particles before and after soaking in SBF can show the formation of carbonated hydroxyapatite. The formation is an indicator for in vitro bioactivity of biomaterials. To study the carbonated hydroxyapatite scanning electron microscopic (SEM) analysis was carried out on a LEO 1530 Gemini (Zeiss, Oberkochen, Germany) after sputtering the samples with ~4 nm of platinum.

Alkaline Capacity:

The alkaline capacity of dense packed material was investigated by titration {Waltimo et al., 2009, J Dent Res, 88, 235-8}. Samples of 1.25 g of nanoparticles or control materials were suspended in 10 ml unbuffered physiological saline to obtain a five times less concentrated suspension compared to the pastes mentioned before. A calibrated pH electrode (Seven Easy, Mettler-Toledo, Greifensee, Switzerland) recorded the continuous titration curve (1.78 ml/h, tubing pump ecoline VC-MS/CA8-6, Switzerland) of 1 molar HCl (Merck, Germany).

Figure 1:
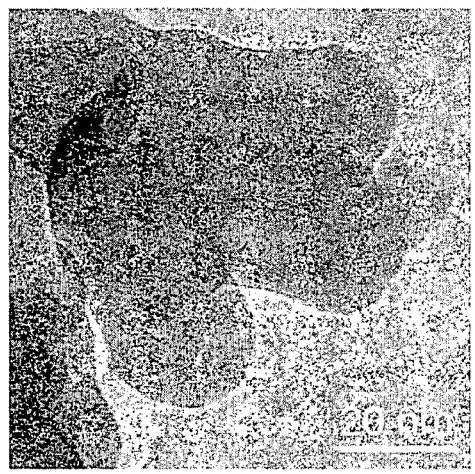
FIG. 1 shows a transmission electron microscopy image of nanometric bioactive particles, according to the prior art (BG45S5).
Figure 2:
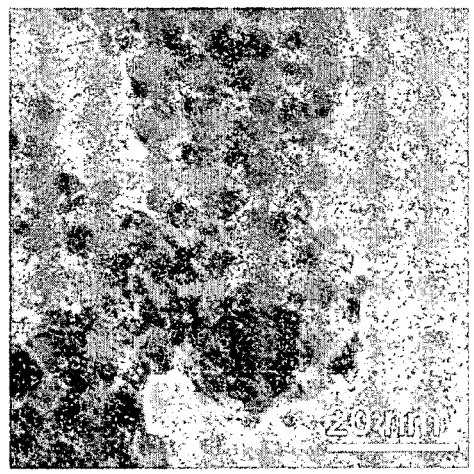
FIG. 2 shows a transmission electron microscopy image of nanometric bioactive particles containing 50 wt % bismuth oxide, according to the invention. As can be seen, bismuth oxide is homogeneously distributed in/on the particles.

Results:

Flame spray synthesis resulted in spherically and highly agglomerated bioactive nanoparticles. The SSA using BET showed that produced bioactive nanoparticles had 71 m2/g while doping the nanoparticles with bismuth oxide reduced it to 60 m2/g and 51 m2/g for nanoparticles with 20 wt % and 50 wt % bismuth oxide, respectively (Table 1). Transmission electron microscopy confirmed the morphology and size of the novel bioactive particles to be in the nanometer range and showed that bismuth oxide was also doped onto the particles' surface (FIGS. 1 and 2).

Pressing the material with uniaxial pressure compacted the powder by a factor of three, resulting in a homogenous powder. The radiopacity of the applied pastes differed strongly from each other (FIG. 3) depending on the amount of radio-opaque agent and doping of bismuth oxide. Pure calcium hydroxide had an aluminum equivalent of 0.6 mm whereas the addition of barium sulphate at a similar ratio to commercially available products (50 wt %) resulted in 2.5 mm. Classical nanometric bioactive particles showed an aluminum equivalent of 0.1 mm; the mechanical mixture with barium sulphate increased this value to 2.2 mm. A mechanical mixture with 20 and 50 wt % bismuth oxide increased the aluminum equivalent to 1.2 mm and 4.7 mm, respectively. Doping the bioactive glass with 20 wt % bismuth oxide in the flame spray process increased the radiopacity to 1.8 mm. An increased bismuth oxide quantity up to 50 wt % resulted in 4.9 mm aluminum equivalents.

The formation of a carbonated hydroxyapatite layer on the surface of bioactive nanoparticles was confirmed using Raman spectroscopy (FIG. 5). It was observed that the bismuth oxide-doped bioactive particles formed a hydroxyapatite layer also.

The alkaline capacity of compacted bioactive particles was lower than that of calcium hydroxide although the initial pH value was in the same range. Adding barium sulphate to calcium hydroxide to render the powder radio-opaque reduced the alkaline capacity by half. Bioactive particles with 20 wt % bismuth oxide (flame derived) showed the same titration curve as classical bioactive glass. The glass containing 50 wt % bismuth oxide (flame derived) had a faster pH drop in comparison to the counterpart with 20 wt % bismuth oxide. However, the incorporation of 50 wt % bismuth oxide using flame-spray synthesis into the bioactive glass reduced alkaline capacity less than mechanically adding either 50 wt % barium sulphate or 50 wt % bismuth oxide.

TABLE 1

Nominal composition of different nanoparticulate bioactive glasses (BG) in wt-%, specific surface area (SSA) and particle size.

| | Particle size$^a$ [nm] | $SiO_2$ | $Na_2O$ | CaO | $P_2O_5$ | $Bi_2O_3$ | SSA$^b$ [m$^2$/g] |
|---|---|---|---|---|---|---|---|
| (BG 45S5) | 34 | 45.0 | 24.5 | 24.5 | 6.0 | — | 71 |
| ex. 2 (BG 45S5 + 20 wt % Bi2O3) | 26 | 36.0 | 19.6 | 19.6 | 4.8 | 20.0 | 60 |
| ex. 3 (BG 45S5, 50 wt % Bi2O3) | 21 | 23.4 | 12.8 | 12.8 | 3.1 | 47.9 | 51 |

$^a$BET equivalent particle diameter, calculated by $\frac{6}{SSA \cdot \rho_{BG}}$;

$^b$Error ±10%

Starting Materials

The preparation of the following precursors is similar to the preparation in WO2004/103900 A1. Precursors like sodium 2-ethylhexanoate and/or calcium 2-ethylhexanoate can be prepared similar to the following description without limiting to this preparation method. 832.15 g Calcium hydroxide (Riedel-de Haen) is dissolved in 9551.4 g 2-ethylhexanoic acid and heated up to 130° C. to yield a final calcium concentration of 4.5 wt %.

EXAMPLE 1

9.71 g hexamethyldisiloxane (ABCR Chemicals), 56.85 g sodium 2-ethylhexanoate (5.11 wt % Na), 50.22 g calcium 2-ethylhexanoate (5.57 wt % Ca), 3.60 g tributyl-phosphate (Acros Organics) and 57.91 g barium 2-ethylhexanoate (6.29 wt % Ba) were homogenously mixed and diluted with 154.8 g xylene to a final volume of about 360 ml. The solution was filtrated and used subsequently. The solution was pumped (5 ml min-1) through a capillary (0.4 mm diameter), dispersed with oxygen (5 l min-1) and ignited with a methane (1.13 l min-1)/oxygen (2.4 l min-1) flame. The as formed particles were collected on a fibre filter (25.7 cm diameter) above the flame with the aid of a vacuum pump. After 60 minutes, 6.5 g of particles were collected. XRD analysis confirmed amorphous material. BET analysis confirmed a SSA of 64 m2/g.

EXAMPLE 2

9.73 g hexamethyldisiloxane (ABCR Chemicals), 61.10 g sodium 2-ethylhexanoate (4.76 wt % Na), 50.30 g calcium 2-ethylhexanoate (5.57 wt % Ca), 3.60 g tributyl-phosphate (Acros Organics) and 12.81 g bismuth 2-ethylhexanoate (28 wt % Bi) were homogenously mixed and diluted with 256.40 g xylene to a final volume of about 450 ml. The solution was filtrated and used subsequently. The solution was pumped (5 ml min-1) through a capillary (0.4 mm diameter), dispersed with oxygen (5 l min-1) and ignited with a methane (1.13 l min-1)/oxygen (2.4 l min-1) flame. The as formed particles were collected on a fibre filter (25.7 cm diameter) above the flame with the aid of a vacuum pump. The particles were sieved (0.315 mm) to yield 10.39 g of a homogenous powder. XRD analysis confirmed amorphous material; further analytical data are provided in table 1. 1 g as prepared powder was uniaxially pressed (2.6 MPa) with the aid of a hydraulic press and grinded subsequently. For the radiopacity assessment 0.2 g of pressed material was homogenously mixed with 0.265 ml saline (0.9 wt % NaCl, Braun) with the aid of a glass plate and spatula. The paste was placed in a polycarbonate mould (1 cm diameter, 0.1 cm high) on a radiographic film (Digora, Finland) together with an aluminum step-wedge with a variable thickness from 0.5 mm to 6 mm (0.5 mm and 1 mm increments). A Trophy Irix (Trophy, Paris, France) X-ray unit operating at 65 kV, 8 mA and 0.22 s with a focus-film distance of 25 cm was used. Digital radiographic images were imported with a Digora system (Soredex, Finland), using Digora software for Windows without grey scale correction. Optimas imaging analysis software (Meyer Instruments Inc., Houston, Tex., USA) was used to determine the mean gray value of the samples and converted the mean gray value to millimeters of aluminum equivalent.

EXAMPLE 3

9.51 g hexamethyldisiloxane (ABCR Chemicals), 59.72 g sodium 2-ethylhexanoate (4.76 wt % Na), 60.72 g calcium 2-ethylhexanoate (4.51 wt % Ca), 3.52 g tributyl-phosphate (Acros Organics) and 46.00 g bismuth 2-ethylhexanoate (28 wt % Bi) were homogenously mixed and diluted with 285.00 g xylene to a final volume of about 480 ml. The solution was filtrated and used subsequently. The solution was pumped (5 ml min-1) through a capillary (0.4 mm diameter), dispersed with oxygen (5 l min-1) and ignited with a methane (1.13 l min-1)/oxygen (2.4 l min-1) flame. The as formed particles were collected on a fibre filter (25.7 cm diameter) above the flame with the aid of a vacuum pump. After 50 minutes, 7.14 g of particles were collected. XRD analysis confirmed amorphous material; further analytical data are provided in table 1.

2 g of the as prepared particles were uniaxially pressed (2.6 MPa) with the aid of a hydraulic press and grinded subsequently. 1.2 g of this material was mixed with 10 ml saline (0.9 wt % NaCl, Braun) and titrated with 1 molar hydrochloric acid and a continuous flowrate of 1.78 ml hour-1 giving the alkaline capacity.

EXAMPLE 4

(Formulation Polymer) A formulation comprising of polyisoprene in an amount of about 30%, zinc oxide in an amount of about 45%, and radio-opaque bioactive glass, according to ex. 2 or 3 respectively, in an amount of about 25% was manufactured. The formulation was manufactured by heating polyisoprene to about 55° C. The other components were then added and mixed by kneading and pressing until a homogenous dough of the formulation is obtained. The dough can be further used on any carrier or as post, tack, pin.

|  | Polyisoprene | ZnO | Radio-opaque BG according to ex. 2 or 3 |
|---|---|---|---|
| Amount | 50 g | 75 g | 42 g, according to ex. 2 |
| Amount | 50 g | 75 g | 42 g, according to ex. 3 |

EXAMPLE 5

(Formulation Suspension) A formulation comprising of 50% radio-opaque bioactive glass, according to ex. 2 or 3 respectively, and 50% of a physiologically saline solution was manufactured. The formulation was mixed by a spatula on a glass plate until a homogenous mixture was reached. The paste may be applied by a rotating instrument.

The invention claimed is:

1. A radio-opaque bioactive glass particle, with a diameter below 200 nm, comprising a matrix and a radiopacifier embedded therein, wherein
   a. said matrix contains oxides of Si, Ca, Na and P; and
   b. said radiopacifier is $Bi_2O_3$;
   and the amount of radiopacifier is 5-50 wt % based on the weight of the particle.

2. The particle according to claim 1, wherein the matrix
   a. contains 20-60 wt % $SiO_2$, 10-50 wt % CaO; 5-50 wt % $Na_2O$; 3-20 wt % $P_2O_5$;
   b. the ratio Ca:P is in the range of 10:1 to 1:10; and
   c. the ratio Ca:Na is in the range of 2:1 to 0.5:1.

3. The particle according to claim 1, additionally containing a coating.

4. The particle according to claim 3 wherein said coating comprises:
   a. functionalized molecules with a molecular mass below 2000 g/mol or
   b. polymers with a molecular mass above 2000 g/mol.

5. A composition containing a plurality of particles according to claim 1.

6. A composition containing a plurality of particles according to claim 3.

7. A formulation comprising particles according to claim 1 and one or more excipients.

8. A formulation comprising particles according to claim 3 and one or more excipients.

9. A formulation comprising particles according to claim 5 and one or more excipients.

10. A formulation comprising particles according to claim 6 and one or more excipients.

11. A formulation according to claim 10 wherein said excipients are selected from the group consisting of aqueous solutions and polymers.

12. The formulation according to claim 11, wherein said aqueous solution is a pharmaceutically acceptable solution and/or a physiologically acceptable antiseptic solution.

13. The formulation according to claim 11 wherein said polymer is selected from the group consisting of biodegradable polymers.

14. The formulation according to claim 11 wherein said polymer is selected from the group consisting of non-biodegradable polymers.

15. A method of manufacturing a particle according to claim 1 comprising the step of:
   subjecting one or more combustible solutions to a flame spray pyrolysis, wherein said one or more solutions contain (i) one or more soluble silica precursors, (ii) one or more soluble sodium precursors, (iii) one or more soluble calcium precursors, (iv) one or more soluble phosphorous precursors, and (v) one or more soluble bismuth precursors.

16. A method of manufacturing a composition comprising the step of (i) providing one or more types of particles as defined in claim 1 and optionally one or more further nanoparticles, (ii) compressing these particles to obtain a composition having a bulk density of at least 0.3 $g/cm^{-3}$.

17. A method of manufacturing a composition comprising the step of combining a plurality of particles as defined in claim 1 with one or more excipients.

18. A disinfectant formulation comprising the composition of claim 6.

19. A dental filling material comprising the composition of claim 6.

20. A method of treating a dental disease, comprising the step of applying an effective amount of a composition according to claim 6 to a subject in need thereof.

21. A composition containing a plurality of particles according to claim 1 and further particles with a diameter below 200 nm.

22. The composition according to claim 21 wherein said further particles are ZnO particles.

23. A composition containing a plurality of particles according to claim 3 and further particles with a diameter below 200 nm.

24. The composition according to claim 23 wherein said further particles are ZnO particles.

* * * * *